(12) United States Patent
Wolf et al.

(10) Patent No.: US 8,709,526 B2
(45) Date of Patent: Apr. 29, 2014

(54) USE OF A HIGH-OLEIC AND HIGH-TOCOL DIET IN COMBINATION WITH A NON-TOCOL ANTIOXIDANT FOR IMPROVING ANIMAL MEAT QUALITY

(75) Inventors: Fred R. Wolf, Urbandale, IA (US); Cindi S. Zimmermann, Madrid, IA (US); Court A. Saunders, Clive, IA (US)

(73) Assignee: E.I. duPont de Nemours and Company, Wilmington, DE (US)

( * ) Notice: Subject to any disclaimer, the term of this patent is extended or adjusted under 35 U.S.C. 154(b) by 1764 days.

(21) Appl. No.: 11/530,075

(22) Filed: Sep. 8, 2006

(65) Prior Publication Data
US 2007/0059344 A1    Mar. 15, 2007

Related U.S. Application Data

(60) Provisional application No. 60/596,256, filed on Sep. 12, 2005.

(51) Int. Cl.
*A23K 1/00*      (2006.01)
*A23K 1/18*      (2006.01)

(52) U.S. Cl.
USPC ............ 426/635; 424/442; 514/458; 514/547

(58) Field of Classification Search
USPC .................... 424/442; 514/458, 547; 426/635
See application file for complete search history.

(56) References Cited

U.S. PATENT DOCUMENTS

| | | | | |
|---|---|---|---|---|
| 5,017,397 | A * | 5/1991 | Nguyen et al. ................. 426/542 |
| 6,242,013 | B1 * | 6/2001 | Luhman et al. .................... 426/2 |
| 6,248,939 | B1 * | 6/2001 | Leto et al. ................... 800/320.1 |
| 6,372,965 | B1 * | 4/2002 | Lightner et al. ............... 800/298 |
| 6,977,269 | B1 * | 12/2005 | Saunders et al. .............. 514/458 |
| 7,154,029 | B2 * | 12/2006 | Cahoon et al. ................ 800/320 |

FOREIGN PATENT DOCUMENTS

CA     2279054 A1 * 2/2000

OTHER PUBLICATIONS

Miller et al. J. Anim. Sci., vol. 68, pp. 1624-1631, 1990.*
Sanchez-Escalante et al. Journal of Food Science, vol. 68, No. 1, pp. 339-344, 2003.*
Buckley et al. J. Anim. Sci. vo. 73, pp. 3122-3130, 1995.*
Cahoon et al. Nature Biotechnology, vol. 21, No. 9, Sep. 2003, pp. 1082-1087.*
Zanardi et al., Oxidative Stability and Dietary Treatment with Vitamin E, Oleic Acid and Copper of Fresh and Cooked Pork Chops, Meat Science (1998) 49(3):309-320.
Bosi et al., Effects of dietary high-oleic acid sunflower oil, copper and vitamin E levels on the fatty acid composition and the quality of dry cured Parma ham, Meat Science (2000) 54:119-126.
Lauridsen et al., Antioxidative and Oxidative Status in Muscles of Pigs Fed Rapeseed Oil, Vitamin E, and Copper, Journal of Animal Science (1999) 77:105-115.
Soler-Velasquez et al., Effects of Supplemental Vitamin E and Canola Oil on Tissue Tocopherol and Liver Fatty Acid Profile of Finishing Swine, Journal of Animal Science (1998) 76:110-117.

* cited by examiner

*Primary Examiner* — Chhaya Sayala

(57) ABSTRACT

A novel method for improving the meat quality of an animal is provided. In one embodiment, the method comprises feeding the animal a diet supplemented with oleic acid and tocols and subsequently formulating the meat with a non-tocol antioxidant such as rosemary extract. The source of the oleic acid and/or tocols may be transgenic corn that employs the FAD-2 gene as a silencing agent for a high-oleic phenotype and/or expresses the HGGT gene for a high-tocotrienol phenotype. The method improves the quality of meat from both non-ruminants and ruminants.

18 Claims, No Drawings

USE OF A HIGH-OLEIC AND HIGH-TOCOL DIET IN COMBINATION WITH A NON-TOCOL ANTIOXIDANT FOR IMPROVING ANIMAL MEAT QUALITY

CROSS-REFERENCE TO RELATED APPLICATIONS

This application claims the benefit of U.S. Application Ser. No. 60/596,256 filed Sep. 12, 2005, which is herein incorporated by reference.

FIELD OF THE INVENTION

This patent relates to a method of improving animal meat quality. More specifically, this patent relates to a method of improving animal meat quality by use of a high-oleic and high-tocol animal diet in combination with an additional non-tocol antioxidant such as rosemary extract to achieve a greater improvement in meat oxidative stability than can be achieved with dietary high-oleic and high-tocol or the additional non-tocol antioxidant alone.

BACKGROUND

The oxidative stability of raw meat and cooked meat products is of great importance to the livestock and meat processing industries. At present, freezing, antioxidant supplementation, and packaging are the primary methods for deterring oxidative deterioration of cooked meat products. However, these methods—whether used alone or in combination—do not necessarily provide adequate initial product quality or shelf life. Cooked meat products in particular are vulnerable to the development of warmed over flavor (WOF) which is largely a consequence of lipid oxidation. This deterioration can result in the development of off-flavors that render the product unpalatable and unsalable.

The antioxidant rosemary extract (RE) is currently used by meat processors to improve meat oxidative stability, especially in precooked products. Commercially available rosemary extracts are generally added to the meat product prior to cooking, and can result in improved initial product quality (e.g., flavor and color) and increased shelf life.

Pioneer Hi-Bred International, Inc. previously has demonstrated that meat derived from animals fed a high oleic-acid/high-tocol (HO/HT) diet exhibits improved meat quality, including oxidative stability. (See U.S. patent Ser. No. 11/153,463 herein incorporated in it's entirety by reference.) Applicants have demonstrated that cooked meat derived from animals fed a high oleic/high tocol diet and subsequently formulated with a non-tocol antioxidant (NTAO) such as rosemary extract (RE) exhibits greater oxidative stability than meat derived from animals fed a high oleic/high tocol diet alone. We have further demonstrated that RE also improves the oxidative stability of meat derived from animals fed either a HO or HT diet.

Thus it is an object of the present invention to provide a method for improving the tissue quality of an animal with respect to meat quality.

It is a further object to improve the quality of precooked meat product, especially its appearance (as measured by color), sensory characteristics and oxidative stability.

A further object of the invention is to provide a method for improving fresh and precooked meat shelf life that is a more desirable alternative or a complement to existing refrigeration and packaging methods.

A still further object of the invention is to provide a method of improving meat quality comprising supplementing the animal feed with both oleic acid and tocols and then treating the meat with certain other non-tocol antioxidants such as rosemary extract.

Further and additional objects will appear from the description and appended claims.

SUMMARY OF THE INVENTION

The present invention is a method for improving meat quality, especially the quality of precooked meat products. The method comprises feeding the animal a diet including elevated levels of oleic acid and selected tocols and subsequently adding a non-tocol antioxidant to the fresh meat. The quality of the meat may be measured in numerous ways, including but not limited to color, flavor and oxidative stability.

The animal diet should comprise at least about 3% total dietary oil (e.g., from corn grain, oilseeds and/or added oil) with oleic acid comprising at least about 50% of the fatty acid fraction and at least about 50 ppm tocols with the subsequent addition of a non-tocol antioxidant (NTAO) to the fresh meat during processing.

In one embodiment, the diet can comprise about 10% total dietary oil (e.g., from corn grain, oilseeds and/or added oil) with oleic acid comprising about 70% of the fatty acid fraction and 150 ppm tocols with the subsequent addition of a non-tocol antioxidant (NTAO) to the fresh meat during processing. In another embodiment, the tocol content can be 500 ppm.

The oleic acid may be in the form of vegetable oil having an elevated level of oleic acid, including, but not limited to: high oleic corn, sunflower, soybean, cotton, cocoa, peanut, safflower, or canola oil. The oleic acid may also be fed in the form of oilseed or grain crops arising from plants genetically modified to confer a high-oleic trait.

Other possible sources of dietary oleic acid are fats or oils with an iodine value comparable to or lower than a high-oleic vegetable oil such as, but not limited to, high-oleic sunflower oil.

The dietary tocols may be one of the tocopherols or tocotrienols or a mixture of tocopherols and/or tocotrienols. The tocotrienols may be a mixture of two or more of the four known tocotrienols or a single tocotrienol. The tocotrienols may be in the form of a distillate obtained from seed processing. The tocotrienols may also be fed in the form of oilseed or grain crops arising from plants genetically modified to confer a high tocotrienol trait.

The genetically modified oilseed or grain used as a source of oleic acid and/or tocols may be modified by transgenic methods well known in the art, including but not limited to: (1) electroporation (see Riggs et al. (1986) Proc. Natl. Acad. Sci. USA 83: 5602-5606; D'Halluin et al. (1992) Plant Cell 4: 1495-1505), (2) *Agrobacterium*-mediated transformation (see Townsend et al., U.S. Pat. No. 5,563,055; and Zhao et al., U.S. Pat. No. 5,981,840), (3) direct gene transfer (see Paszkowski et al. (1984) EMBO J. 3: 2717-2722), and (4) ballistic particle acceleration (see, for example, Sanford et al., U.S. Pat. No. 4,945,050; Tomes U.S. Pat. No. 5,240,855; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); and McCabe et al. (1988) Biotechnology 6: 923-926); including ballistic particle acceleration of a gene and an LEC1 construct as a transcriptional activator (see International Patent Publication No. WO 00/28058).

For references describing transformation of specific plant species, see Sanford et al. (1987) Particulate Science and Technology 5: 27-37 (onion); Christou et al. (1988) Plant Physiol. 87: 671-674 (soybean); McCabe et al. (1988) Bio/Technology 6: 923-926 (soybean); Finer and McMullen (1991) In Vitro Cell Dev. Biol. 27P: 175-182 (soybean); Singh et al. (1998) Theor. Appl. Genet. 96: 319-324 (soybean); Datta et al. (1990) Biotechnology 8: 736-740 (rice); Klein et al. (1988) Proc. Natl. Acad. Sci. USA 85: 4305-4309 (maize); Klein et al. (1988) Biotechnology 6: 559-563 (maize); Buising et al., U.S. Pat. Nos. 5,322,783 and 5,324,646; Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al. (1988) Plant Physiol. 91: 440-444 (maize); Fromm et al. (1990) Biotechnology 8: 833-839 (maize); Hooykaas-Van Slogteren et al. (1984) Nature (London) 311: 763-764; Bowen et al., U.S. Pat. No. 5,736,369 (cereals); Bytebier et al. (1987) Proc. Natl. Acad. Sci. USA 84: 5345-5349 (Liliaceae); De Wet et al. (1985) in The Experimental Manipulation of Ovule Tissues, ed. Chapman et al. (Longman, N.Y.), pp. 197-209 (pollen); Li et al. (1993) Plant Cell Reports 12: 250-255 and Christou and Ford (1995) Annals of Botany 75: 407-413 (rice); Osjoda et al. (1996) Nature Biotechnology 14: 745-750 (maize via *Agrobacterium tumefaciens*).

The genetically modified oilseed or grain used as a source of oleic acid and/or tocols can also be modified by means of naturally occurring or induced mutations. See, for example, Bensen et al. (1995) Plant Cell 7:75-84; Mena et al. (1996) Science 274:1537-1540; U.S. Pat. No. 5,962,764; Ohshima, et al. (1998) Virology 243:472-481; Okubara et al. (1994) Genetics 137:867-874; Quesada et al. (2000) Genetics 154: 421-436 and McCallum et al. (2000) Nat. Biotechnol. 18:455-457).

Preferably, the oleic acid and the tocols are added to the feed in the form of a corn grain arising on ears of corn plants that employ the FAD-2 gene as a silencing agent for a high-oleic phenotype and/or express HGGT genes for high-tocotrienol phenotype (see U.S. Pub. 2004-0034886A1 and U.S. Pat. No. 6,372,965). These and all other references cited herein are hereby expressly incorporated into this document in their entirety by reference.

Preferably, the NTAO is rosemary extract (RE) or any other antioxidant preparation derived from the rosemary species (*Rosemarinus officinalis*) such as carnosol or rosemaric acid. However, other non-tocol antioxidants may be used, including but not limited to any of the following:

(1) Flavanoids (or bioflavonoids). A group of about 4,000 polyphenolic compounds widely distributed in plants including anthocyanins (found in bilberry leaves and other places), catechin (a tea extract), curcumin (turmeric pigment), genistein (found in soybeans), kaempferol (found in numerous fruits and vegetables, including apples, onions, leeks, citrus fruits and grapes), myrocetin (found in berries and other fruits), quercetin (found in numerous natural sources), Pycogenol® (found in pine bark, particularly the bark of the French maritime pine tree) and rutin (found in buckwheat and other plants, as well as extracts from cranberries, elderberry, grape seeds, huckleberries and sage.

(2) Hydroxycinnamic and hydroxybenzoic acids. Monocyclic compounds also widely distributed in plants. Hydroxycinnamic acids (phenylpropanoids) include caffeic, ferulic and sinapic acids. Hydroxybenzoic acids include salicylic acid and gallic acids.

(3) Carotenoids, including the carotenes (e.g. beta-carotene and lycopene) and the xanthophylls (e.g. lutenin and zeaxanthin).

(4) Alpha-lipoic acid.

(5) Ascorbic acid.

(6) Other antioxidants, including synthetic antioxidants such as butylated hydroxytoluene (BHT) and butylated hydroxyanisole (BHA), tertiary butyl hydroquinone (TBHQ), peptides (e.g. cansine and glutathione (a tripeptide)), melatonin, amino acid derivatives (e.g. sesaminol and sesamol), reseveratrol (found in red wine) and sodium nitrite.

Antioxidants that function at least in part as transition metal chelators (e.g. those which contain phenyl groups with ortho-hydroxyl groups such as quercetin) may be particularly useful in this invention.

The animal may be a non-ruminant, including, but not limited to, swine, poultry or fish, or a ruminant, including, but not limited to, cattle or lamb.

DETAILED DESCRIPTION OF THE INVENTION

The present invention is a novel method for improving the tissue quality of an animal, the method comprising feeding the animal a high oleic/high tocol diet and then treating the meat with a non-tocol antioxidant such as rosemary extract in amounts effective to improve the tissue quality. The animal diet should comprise at least about 3% total dietary oil (e.g., from corn grain, oilseeds and/or added oil) with oleic acid comprising at least about 50% of the fatty acid fraction and at least about 50 ppm tocols with the subsequent addition of a non-tocol antioxidant (NTAO) to the meat during processing.

In one embodiment, the diet can comprise about 10% total dietary oil (e.g., from corn grain, oilseeds and/or added oil) with oleic acid comprising about 70% of the fatty acid fraction and 150 ppm tocols with the subsequent addition of a non-tocol antioxidant (NTAO) to the fresh meat during processing. In another embodiment, the tocol content can be 500 ppm.

In the examples that follow, meat quality is measured as oxidative stability (TBARS level). The method has been proven effective with swine and cattle, and is expected to be effective with other non-ruminants and ruminants.

Definitions

Throughout this patent application a number of terms and abbreviations are used. The following definitions are provided to assist the reader:

Alpha-tocopherol acetate (ATA) is the synthetic form of alpha-tocopherol, the most commonly used antioxidant in the livestock industry.

Control (CO) refers to a control dietary treatment.

High-oleic diet (HO) refers to a diet having an elevated level of oleic acid.

High-oleic trait: a trait wherein the genetically modified oilseed or grain exhibits a greater than wild-type level of oleic fatty acid. See WO Pub. 94/11516, WO Pub. 90/10380, WO Pub. 91/11906, and U.S. Pat. No. 4,627,192.

High-tocol diet (HT): a diet having an elevated level of tocols.

Malonaldehyde (MDA): a TBARS analyte found in many foodstuffs and often used in research as a measure of rancidity (oxidative stability). Non-Tocol Antioxidant (NTAO): any antioxidant that is not a tocol.

Rosemary extract (RE): a mixture of natural compounds present in the rosemary plant (*Rosemarinus officinalis*) whose antioxidant properties retard the oxidation of lipids. It is added to processed meats to retard oxidation.

Thiobarbituric acid reactive substances (TBARS) concentration in meat is used as a measure of the extent of oxidation.

Tocols (or Vitamin E): two groups of lipophilicantioxidants (tocopherols and tocotrienols) that consist of a 6-chromanol ring fused to an isoprenoid-derived sidechain.

The four naturally occurring tocopherols, designated as alpha-, beta-, gamma-, and delta-, differ from one another only with respect to the number and position of methyl groups on the 6-chromanol ring. The four naturally occurring tocotrienols, also designated alpha-, beta-, gamma- and delta- are relatively abundant in certain cereals (including barley, maize and rice) and vegetable oils such as, but not limited to, palm and grapeseed. Tocotrienols are identical to their tocopherol counterparts except that the isoprenoid-derived sidechain contains three double bonds versus the completely saturated side chains of tocopherols. As used herein the terms "tocotrienols" and "T3" refer to a mixture of two or more tocotrienols or a single tocotrienol. The T3 mixture may contain other components, including tocopherols.

EXAMPLES

The present invention is further defined by the following examples. The examples, while indicating particular embodiments of the invention, are given by way of illustration only. From the discussion contained herein and the examples themselves, one skilled in the art can ascertain the essential characteristics of the invention and, without departing from the scope thereof, make changes and modifications to the invention to adapt it to various situations and conditions.

In the examples that follow, the oleic acid additive amounts are expressed as a percentage of the total fatty acid fraction. The alpha-tocopherol acetate (ATA) and tocotrienol (T3) additive amounts are expressed as weight parts additive per million weight parts feed (ppm).

Example 1

Demonstration that Cooked Pork Derived from Swine Fed a High-Oleic/High-Tocol Diet and Subsequently Formulated with Rosemary Extract (RE) Exhibits Improved Oxidative Stability Applicants assessed the effect on the oxidative stability of pork (as measured by TBARS concentration) of supplementing the swine diet with oleic acid and tocols and subsequently formulating the pork with rosemary extract. Swine were fed one of four dietary treatments as follows:

TABLE 1

| SWINE DIETARY TREATMENTS | |
| --- | --- |
| Group | Treatment |
| 1 | CO |
| 2 | HO |
| 3 | HO + 300 ppm ATA |
| 4 | HO + 300 ppm T3 |

In the group 1—control (CO)— diet, the total dietary content of oil was 5.5 wt % of the feed. The oil was a typical corn oil having an oleic acid content of 29.6% oleic acid content.

In group 2, the high-oleic acid (HO) diet, the total dietary content of oil was still 5.5 wt %, but the oil was high-oleic sunflower oil with an oleic acid content of 80.2%.

The group 3 diet was supplemented with sunflower oil to simulate a high oleic acid diet, and further supplemented with 300 ppm ATA.

The group 4 diet was supplemented with sunflower oil to simulate a high oleic acid diet, and further supplemented with 300 ppm T3.

All four experimental diets were formulated with soybean meal and corn flaking grits. The latter, being largely devoid of oil, were used in conjunction with the corn and high-oleic vegetable oils to achieve the desired dietary fatty acid content.

The tocotrienol used to supplement the HO+T3 (group 4) diet was obtained commercially from Fuji Chemical Industries (U.S.A.) Inc. of Robbinsville, N.J., and contained 7.5% alpha-, 12.3% gamma- and 3.0% delta-tocotrienol (a total tocotrienol content of 22.8%), as well as 7.2% alpha-tocopherol.

The pigs were slaughtered and the carcasses processed to provide the ground pork used in this study. Samples of raw ground pork from all four dietary groups, as well as samples of raw ground pork from groups 1 and 4 that had been further formulated with 0.2% wt % rosemary extract (RE) (Herbalox seasoning, type HT-25, Kalsec Inc., Kalamazoo, Mich.), were shaped into patties, cooked, and refrigerated for 24 hours. The precooked refrigerated ground pork were submitted for TBARS determination at 0 hours and 24 hours after refrigeration. The results are given in Table 2 below.

TABLE 2

TBARS CONTENT OF PRECOOKED GROUND PORK PATTIES (mg malonaldehyde[1]/kg sample)

| Group | Treatment | 0 hours | % reduction vs. 0 hr control | 24 hours | % reduction vs 24 hr control |
| --- | --- | --- | --- | --- | --- |
| 1 | Control (CO) | 1.187 | | 3.548 | |
| 1' | CO + RE | 0.853 | 53.05 | 2.36 | 33.48 |
| 2 | HO | 1.37 | 24.60 | 2.648 | 25.37 |
| 3 | HO + 300 ppm ATA | 1.164 | 35.94 | 2.328 | 34.39 |
| 4 | HO + 300 ppm T3 | 1.08 | 40.56 | 1.987 | 44.00 |
| 4' | HO + 300 ppm T3 + RE | 0.571 | 68.57 | 1.206 | 66.01 |

[1]Malonaldehyde is a TBARS analyte.

1. Malonaldehyde is a TBARS analyte.

From Table 2 it can be seen that at 0 hours after refrigeration the precooked patties from the HO+T3+RE group (group 4') exhibited the greatest reduction in TBARS content (68.57%) of all the non-control groups compared to the control (CO) group. At 24 hours after refrigeration precooked patties from all of the non-control groups exhibited improved oxidative stability, as indicated by a lower TBARS value, versus the control group. The greatest improvement in oxidative stability at 24 hour was again exhibited by the HO+T3+RE group, i.e., the group in which the swine diet was supplemented with oleic acid and tocotrienols and the fresh meat subsequently formulated with rosemary extract.

Example 2

Demonstration that Ground Beef Derived from Cattle Fed a High Oleic/High Tocol Diet and Subsequently Formulated with Rosemary Extract (RE) Exhibits Improved Oxidative Stability Applicants assessed the effect on the oxidative stability of beef (as measured by TBARS concentration) of supplementing the cattle diet with oleic acid and tocols and subsequently formulating the fresh meat with rosemary extract prior to cooking. Cattle were fed one of four dietary treatments as shown below:

TABLE 3

CATTLE DIETARY TREATMENTS

| Group | Treatment |
|---|---|
| 1 | CO |
| 2 | HO |
| 3 | 200 ppm T3 |
| 4 | HO + 200 ppm T3 |

In the group 1—control (CO)—diet, the total dietary content of oil was about 6 wt % of the feed. The oil was a typical corn oil having an oleic acid content of 29.6%.

In group 2, the high-oleic acid (HO) diet, the total dietary content of oil was still about 6 wt %, but the oil was high-oleic sunflower oil with an oleic acid content of 80.2%.

The group 3 diet was supplemented with about 200 ppm T3.

The group 4 diet was supplemented with sunflower oil to simulate a high oleic acid diet, and further supplemented with about 200 ppm T3.

The cattle were slaughtered and the carcasses processed to provide the ground beef used in this example. Samples of raw ground beef from all four dietary groups were further formulated with RE, making eight treatment groups altogether. Samples of raw ground beef from all eight groups were shaped into patties and cooked, and refrigerated for 24 hours. The cooked ground beef patties were submitted for TBARS determination at 0 hours and 24 hours after refrigeration. The results are given in Table 4 below.

TABLE 4

TBARS CONTENT OF COOKED GROUND BEEF PATTIES
(mg malonaldehyde[1]/kg sample)

| Group | Treatment | 0 hours | % reduction vs. 0 hr control | 24 hours | % reduction vs 24 hr control |
|---|---|---|---|---|---|
| 1 | Control (CO) | 1.026 | | 1.86 | |
| 1' | CO + RE | 0.6602 | 35.65 | 1.15 | 38.17 |
| 2 | HO | 0.7823 | 23.75 | 1.33 | 28.49 |
| 2' | HO + RE | 0.5515 | 46.25 | 0.93 | 50.00 |
| 3 | 200 ppm T3 | 0.7205 | 29.98 | 1.24 | 33.33 |
| 3' | 200 ppm T3 + RE | 0.4982 | 51.44 | 0.85 | 54.30 |
| 4 | HO + 200 ppm T3 | 0.6451 | 37.12 | 1.15 | 38.17 |
| 4' | HO + 200 ppm T3 + RE | 0.3888 | 62.10 | 0.69 | 62.90 |

[1]Malonaldehyde is a TBARS analyte.

From Table 4 it can be seen that at 0 hours after refrigeration cooked ground beef patties from all of the non-control treatment groups exhibited improved oxidative stability (lower TBARS content) versus the control group. Cooked ground beef patties from the HO+T3+RE group (group 4'), exhibited the greatest reduction in TBARS content (62.10%) of all the non-control groups. At 24 hours after refrigeration, cooked ground beef patties from all of the non-control treatment groups again exhibited improved oxidative stability versus the control group, with the greatest improvement in oxidative stability again exhibited by group 4', the HO+T3+RE group, in which the cattle diet was supplemented with oleic acid and tocols and the fresh meat subsequently formulated with rosemary extract.

Example 3

Demonstration that Beef Fajitas Derived from Cattle Fed a High Oleic/High Tocol Diet and Subsequently Formulated with Rosemary Extract (RE) Exhibits Improved Oxidative Stability Skirt steaks were obtained from the slaughtered cattle fed one of the four dietary treatments listed in Table 3: Control (CO), High-oleic (HO), 200 ppm T3 (T3), and high-oleic plus 200 ppm T3 (HO+T3). Skirt steaks from the CO and HO+T3 dietary treatment groups were formulated with rosemary extract. The source of the RE was Herbalox seasoning, type BP, which does not contain vegetable oils or tocols. The skirt steaks from all six groups were cut into pieces and placed with marinade ingredients into a tumbler. The pieces were then cooked to an internal temperature of about 170 degrees F. and run through a slicer. Slices were then used in the preparation of precooked fajitas which were then refrigerated. Results of TBARS assays on the precooked refrigerated fajitas are presented in Table 5 below.

TABLE 5

COMPARISON OF TBARS CONTENT OF COOKED FAJITAS
(mg malonaldehyde[1]/kg sample)

| | CO | CO + RE | HO | T3 | HO + T3 | HO + T3 + RE |
|---|---|---|---|---|---|---|
| Day 0 | 1.08 | 0.60 | 0.50 | 0.54 | 0.48 | 0.38 |
| Day 7 | 9.04 | 3.43 | 1.31 | 1.13 | 0.51 | 0.95 |
| Day 14 | 8.28 | 4.47 | 1.77 | 1.54 | 0.73 | 0.43 |
| Day 16 | 11.28 | 4.55 | 0.73 | 1.05 | 1.02 | 1.28 |
| Day 21 | 10.54 | 9.24 | 6.02 | 1.33 | 1.54 | 1.29 |
| Day 28 | 10.32 | 6.87 | 5.11 | 11.37 | 0.61 | 3.07 |

[1]Malonaldehyde is a TBARS analyte. A value of 2 is sometimes taken to be a threshold value for the detection of warmed over flavor.

From Table 5 it can be seen that the control treatment exhibited a large increase in TBARS score by day 7, indicating that these samples were likely unpalatable at that point. The CO+RE treatment was somewhat effective up until day 16, although TBARS scores exceeded 2.0 mg MDA/kg sample by day 7. The other four dietary treatments (HO, T3, HO+T3 and HO+T3+RE) resulted in better oxidative stability than the CO+RE treatment through day 21. However, by day 21 the HO treatment had lost some efficacy. At day 28 the HO+T3 group exhibited the greatest oxidative stability at a value of 0.61 mg MDA/kg sample. Cooked fajitas from the HO+T3+RE group exhibited lower TBARS concentration than fajitas from the control group on every testing day and the lowest TBARS concentration of fajitas from all groups on days 0, 14 and 21.

These results indicate that supplementation of cattle diet with both a high-oleic acid oil like sunflower oil and added tocotrienols and then formulating the meat with rosemary extract lowers oxidation in cooked fajitas, thus improving their quality.

Example 4

Demonstration that the Addition of various Non-Tocol Antioxidants To Ground Pork Derived From Swine Fed a High-Oleic/High-Tocol Diet Results IN Improved Oxidative Stability in Precooked, Refrigerated Pork Patties Ground pork from a control group of swine and from swine whose feed was supplemented with sunflower oil (total dietary oil content of 5.5 wt %; 80.2% oleic acid) and 300 ppm T3 ("HO+T3 swine"), as well as ground pork from the HO+T3 swine that was formulated with various non-tocol antioxidants (NTAOs), was shaped into patties, cooked and refrigerated. The precooked, refrigerated patties were submitted for TBARS determination at 0 hours and 24 hours after refrigeration. The results are given in Table 6 below.

TABLE 6

TBARS CONTENT OF PRECOOKED GROUND PORK PATTIES
(mg malonaldehyde/kg sample)

| Group | Treatment | 0 hours | % reduction vs. 0 hr control | 24 hours | % reduction vs 24 hr control |
|---|---|---|---|---|---|
| 1 | Control (CO) | 2.81 | | 4.07 | |
| 2 | HO + T3 | 1.31 | 53.4 | 2.52 | 38.0 |
| 2a | HO + T3 + 500 ppm ascorbic acid | .29 | 90.0 | .61 | 84.9 |
| 2b | HO + T3 + 100 ppm sodium nitrite | .23 | 91.8 | .32 | 92.2 |
| 2c | HO + T3 + 60 ppm BHT | .81 | 71.1 | 1.51 | 62.9 |
| 2d | HO + T3 + 60 ppm BHA | .31 | 89.0 | .30 | 92.6 |
| 2e | HO + T3 + 60 ppm TBHQ | .26 | 90.7 | .25 | 93.8 |
| 2f | HO + T3 + 2000 ppm RE | .35 | 87.5 | .77 | 81.0 |
| 2g | HO + T3 + 100 ppm caffeic acid | .87 | 69.0 | 1.58 | 61.3 |
| 2h | HO + T3 + 40 ppm Carnosic acid | .89 | 68.3 | 1.79 | 56.0 |
| 2i | HO + T3 + 100 ppm rosmarinic acid | 1.06 | 62.3 | 1.81 | 55.5 |

From Table 6 it can be seen that at 0 hours after refrigeration the precooked patties from every non-control group exhibited greater oxidative stability than the control group, with the HO+T3+100 ppm sodium nitrite group (group 2b) exhibiting the greatest improvement in oxidative stability. At 24 hours after refrigeration, precooked patties from all the non-control groups again showed improvement over the control group. The greatest improvement in oxidative stability at 24 hours was the HO+T3+60 ppm TBHQ group (group 2e), i.e., the group in which the swine diet was supplemented with oleic acid and tocotrienols and the fresh pork formulated with 60 ppm tertiary butyl hydroquinone (TBHQ).

CONCLUSIONS

Examples 1-4 demonstrate that supplementation of animal diet with both a high oleic-acid oil such as sunflower oil and tocols, and then formulating the fresh meat with a non-tocol antioxidant enhances the oxidative stability of the meat, thus improving its quality. The improvement has been demonstrated in meat from swine and cattle and is expected to occur in meat from other non-ruminants and ruminants. The feeding and formulating strategy of the present invention has been demonstrated to improve precooked meat products, but it may also be used to improve the quality of fresh meat products. The invention has been demonstrated to be effective at improving oxidative stability of meat but is also expected to improve other meat quality parameters such as flavor and color.

The animal diet should comprise at least about 3% total dietary oil (i.e., from corn grain, oilseed, and/or added oil) with oleic acid comprising at least about 50% of the fatty acid fraction, and at least about 50 ppm tocols, with the subsequent addition of a non-tocol antioxidant.

The oleic acid may be in the form of vegetable oil having an elevated level of oleic acid, such as high-oleic corn, sunflower, soybean or canola oil. The oleic acid may also be in the form of corn grain arising on ears of genetically modified corn.

The tocols may be one of the tocopherols or tocotrienols or a mixture of tocopherols and/or tocotrienols. The tocotrienols may be a mixture of two or more of the four known tocotrienols or a single tocotrienol. The tocotrienols may be in the form of a distillate obtained from seed processing or, as with the oleic acid, transgenically modified corn having an increased tocotrienol concentration.

In one embodiment, the oleic acid and the tocols are added to the feed in the form of a corn grain arising on ears of corn plants that employ the FAD-2 gene as a silencing agent for a high-oleic phenotype and/or express HGGT genes for a high-tocotrienol phenotype.

The NTAO preferably is added to the fresh raw meat (in vitro) but may also be added to the animal feed (in vivo). Preferably, the NTAO is rosemary extract (RE), but any suitable non-tocol antioxidant can be used.

When used to enhance the oxidative stability of precooked meat, the NTAO is preferably added prior to precooking but may also be added after precooking.

Other modifications and alternative embodiments of the invention are contemplated which do not depart from the scope of the invention as defined by the foregoing teachings and appended claims. It is intended that the claims cover all such modifications that fall within their scope.

What is claimed is:

1. A method of improving the meat quality of an animal, the method comprising the steps of:
   a. feeding the animal a diet comprising, (i) 3% to 10% total dietary oil with oleic acid comprising 50% to 70% of the fatty acid fraction of the oil and (ii) 50 ppm to 500 ppm tocotrienols, wherein said diet comprises a genetically modified, high oleic acid and high tocotrienol cereal grain crop or oilseed;
   b. harvesting meat from the animal; and
   c. adding to the meat a non-tocol antioxidant; wherein the meat exhibits improved quality.

2. The method of claim 1 wherein oleic acid comprises at least 70% of the fatty acid fraction.

3. The method of claim 1 or 2 wherein the non-tocol antioxidant is rosemary extract.

4. The method of claim 1 wherein the diet comprises about 150 ppm tocotrienols.

5. The method of claim 1 wherein the diet comprises about 500 ppm tocotrienols.

6. The method of claim 1 wherein the cereal grain crop is corn.

7. The method of claim 1 wherein the oilseed crop is soybean.

8. The method of claim 1 wherein a fatty acid desaturase 2 (FAD-2) gene confers the elevated oleic acid levels and a homogentisate geranylgeranyl transferase (HGGT) gene confers the elevated levels of tocotrienols.

9. The method of claim 1 wherein the animal is a non-ruminant.

10. The method of claim 9 wherein the animal is swine.

11. The method of claim 1 wherein the animal is a ruminant.

12. The method of claim 11 wherein the animal is bovine.

13. The method of claim 1 further comprising the step of measuring the meat quality wherein the quality of the meat is measured by criteria selected from the group consisting of: color, flavor, and oxidative stability.

14. The method of claim 13 wherein the meat is precooked.

15. The method of claim 14 wherein the non-tocol antioxidant is added to meat prior to pre-cooking.

16. The method of claim 14 wherein the non-tocol antioxidant is added to the meat after pre-cooking.

17. The method of claim 1 wherein the dietary oil with oleic acid in the diet comprises high-oleic vegetable oil.

18. The method of claim 17 wherein the high-oleic vegetable oil is selected from the group consisting of: corn oil, sunflower oil, soybean oil, and canola oil.

* * * * *